(12) United States Patent
Arvey

(10) Patent No.: US 9,447,987 B1
(45) Date of Patent: Sep. 20, 2016

(54) VARIABLE AIR ACCESS FILMS

(71) Applicant: Preco, Inc., Somerset, WI (US)

(72) Inventor: Ken Arvey, Somerset, WI (US)

(73) Assignee: Preco, Inc., Somerset, WI (US)

( * ) Notice: Subject to any disclaimer, the term of this patent is extended or adjusted under 35 U.S.C. 154(b) by 363 days.

(21) Appl. No.: 14/266,434

(22) Filed: Apr. 30, 2014

Related U.S. Application Data

(60) Provisional application No. 61/818,241, filed on May 1, 2013.

(51) Int. Cl.
| | | |
|---|---|---|
| *A61F 7/00* | (2006.01) | |
| *F24J 1/00* | (2006.01) | |
| *F23L 13/00* | (2006.01) | |
| *A61F 7/03* | (2006.01) | |

(52) U.S. Cl.
CPC ............... *F24J 1/00* (2013.01); *A61F 7/034* (2013.01); *F23L 13/00* (2013.01)

(58) Field of Classification Search
CPC ............. F24J 1/00; F23L 13/00; A61F 7/03; A61F 7/032; A61F 7/034
See application file for complete search history.

(56) References Cited

U.S. PATENT DOCUMENTS

| | | | | |
|---|---|---|---|---|
| 5,042,455 A | * | 8/1991 | Yue | F24J 1/00 126/204 |
| 6,893,453 B2 | * | 5/2005 | Agarwal | A61F 7/034 607/108 |
| 7,950,385 B2 | * | 5/2011 | Ohnishi | A61F 7/034 126/204 |
| 7,971,585 B2 | | 7/2011 | Bommaraju | |
| 8,205,608 B2 | | 6/2012 | Bommaraju | |
| 2012/0030992 A1 | | 2/2012 | Bommaraju | |
| 2014/0102435 A1 | * | 4/2014 | Sesock | F24J 1/00 126/263.02 |

* cited by examiner

*Primary Examiner* — Alfred Basichas
(74) *Attorney, Agent, or Firm* — Westman, Champlin & Koehler, P.A.; Z. Peter Sawicki; Amanda M. Prose

(57) ABSTRACT

A variable air access mechanism and method of varying air access comprising a first film with a predetermined amount of total air access openings to be formed by removal of laser cut chads; a portion of the chads only partially cut; and a second film adhered to the first film wherein removal of the second film in a first direction opens all of the air access openings or removal of the second film in an opposing direction leaves the partially cut chads attached to the first film such that only selected chads are removed.

11 Claims, 3 Drawing Sheets

VARIABLE AIR ACCESS FILMS

CROSS-REFERENCE TO RELATED APPLICATION

The present application claims the benefit of U.S. provisional patent application Ser. No. 61/818,241, filed May 1, 2013, the content of which is hereby incorporated by reference in its entirety.

FIELD OF THE INVENTION

The present invention relates to laser or mechanical processing of materials, and more particularly to a method of variable air access for air access films.

BACKGROUND

Air activated heat technology, (sometimes referred to as flame-less heat technology or oxidative heat technology) is widely used to heat various products. The air-activated heater is contained in a package such that the heater can be used to heat various contents of a package, or contents in contact with the heater package. In addition the technology can be mechanically attached to thermoformable materials (for example formable splints and braces) to modify the shape using heat transfer. This technology is used in a variety of applications including as a method to heat combat rations, also known as a Meal, Ready to Eat (MRE). The technology is also used in connection with various cold weather activities and can be found in foot and hand warmer inserts as well therapeutic devices as across a variety of other uses.

The prior art method of using air activated heat technology is limited to restricting or increasing air flow by reducing or increasing the size of an outer (removable) barrier layer. Since uniform distribution of air is required for effective utilization of heat, reducing the access area is less effective and can cause hot spots and/or uneven heating.

In many applications where air activated heaters are used, problems arise based on the varying start temperatures. In the instance where air activated heaters are used to heat an MRE or a thermoformable splint or brace the starting temperature maybe be higher or lower than room temperature. For instance, a thermoformable splint used on a ski slope versus has a lower initial temperature than a splint used to help a soccer player on a hot soccer field. Current technology results in uneven heating, insufficient heating and/or burning or hot spots. Present technology does not allow for the same prepared package to be properly heated from varying start temperatures. The start temperature may or higher than intended based on available storage options. This is especially true for military uses of MREs since conditions may not allow for storage of MREs at or near room temperature. If an MRE package is prepared from a higher starting temperature than intended, when air is allowed to access the air activated heater the MRE will burn or otherwise over cook as the user has no control over, or option to reduce the air flow to the heater. Conversely, if an MRE intended to be kept at room temperature is used from a colder starting temperature, the air activated heater may not have enough air access to produce enough heat to fully warm or heat the contents of the package.

SUMMARY

This disclosure includes a variable air access mechanism, the mechanism comprising a first film with a plurality of air access openings; a portion of the air access openings only partially cut; a remainder of the plurality of air access openings substantially fully cut; and a second film adhered to the first film wherein removal of the second film in a first direction opens all of the air access openings or removal of the second film in an opposing direction opens only the fully cut openings.

This disclosure also includes a method of controlling air access to an air activated heater, the method comprising determining a desired amount of total air access openings to be formed; determining a ratio of substantially fully cut air access openings to partially cut air access openings of the total air access openings to be formed; preparing a first film with the determined ratio of air openings; laminating a layer to the first film; and removing the layer in a first or a second direction such that the total air access openings are opened or only the fully cut air access openings are opened.

This disclosure also relates to an air access layer, the layer comprising a film with a plurality of cut chads for subsequent removal to form air access openings; a portion of the chads formed by being only partially cut, wherein the orientation of the partially cut chads is consistent; and a remainder of the plurality of cut chads being substantially fully cut.

DETAILED DESCRIPTION

When using air activated heating technology to heat a product, air access needs to be adjusted to account for the heat transfer effects of the target product, which can be based on the starting temperature of the product. This invention provides a solution to the variable air access problem by using mechanical processing methods, laser processing or a similar converting technology to create a film that allows a user to vary the air access. The mechanical processing methods include hard tooling cutting methods such as use of rotary die cutter or a flatbed die cutter or any suitable form of mechanical cutting.

This disclosure relates to a multi-direction air access feature for an air access heater. As illustrated generally in FIG. 1 at 10, a film is described herein that has the capability of varying the amount of air access to an air activated heater through selective cutting by mechanical processing or laser processing an air access film. The terms "mechanical" and "die" cutting and processing are used throughout this specification to refer to a mechanically formed cut. A laser beam may also be used to selectively cut air access openings in an air access film.

The air access film disclosed in this application can be used to control air access across a variety of uses including, but not limited to, thermoformable splints and/or braces, with various types of heating pads, portable, reusable and/or single use heating devices for muscle aches and body pains, food containers for storage and/or heating of prepared and/or fresh food.

Additionally, the air access film and air activated heating device 10 as described throughout this disclosure can be used in a product comprising a fuel source and as such, a heating mechanism. However, the air access film can also be used in applications without a fuel source, such as in constructing fresh food packaging for storage or preparation for all types of foods including but not limited to fresh, frozen and/or prepared fruits, vegetables, breads and meats or fish to control air flow within and into and out of the packaging.

Figure 2:
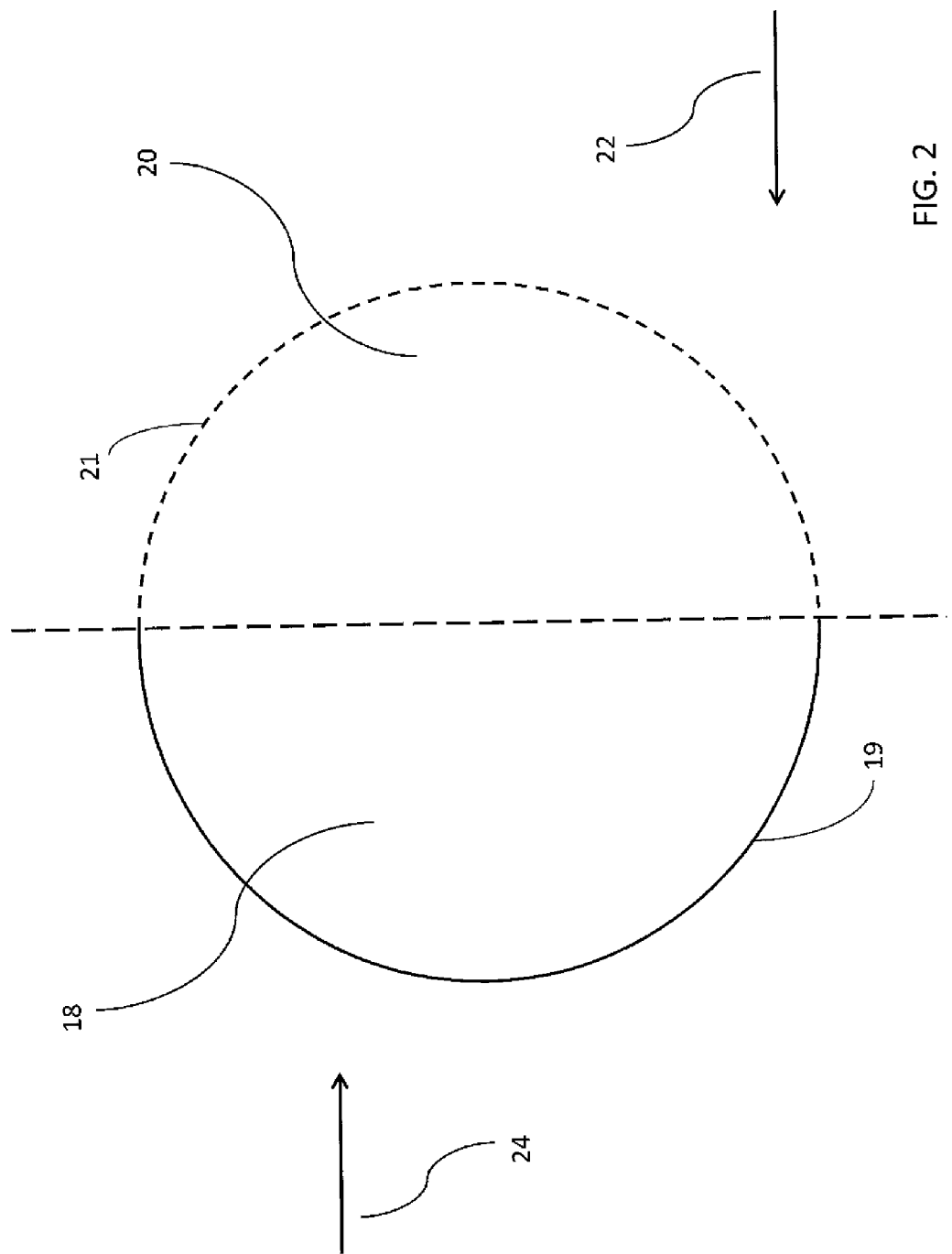
FIG. 2 is a top view of an individual processed chad in the prepared film.

The die cutter or laser beam is used to cut chads that are selectively removable by a barrier film 6 adhesively secured to the air access film 8 such that when the chads are removed, air access openings are formed in the air access film 8. By the word "chad" is meant an area of the film cut by mechanical cutting or the laser processing for subsequent removal to form an air access opening. A first selected amount of through cut chads 14 are cut such that the through cut chads 14 are removable when the barrier film 6 is separated from the air access film 8. As illustrated in further detail in FIG. 2, a second selected amount of partially score cut chads 16 are cut such that a first portion 18 of the cut that forms the chad is a through cut through the film 8. Solid line 19 of the circumference represents the fully through cut portion. The remaining portion 20 of the cut that defines the chad 16 is a score cut as represented by the dashed circumference line 21. The partially score cut chads 16 are oriented such that the partially score cut chads 16 are aligned in parallel arrangement with the score cut portions 20 all facing the same direction. Thus when the barrier film 6 is separated from the air access film 8 by pulling on the barrier film 6 in a first direction 22 in which partially score cut chads 16 are each initially pulled on the score cut portion 20 of the chad, the through cut chads 14 are completely removed from the air access film 8 while leaving the partially score cut chads 16 still secured to the air access film 8. Pulling the barrier film 6 in the first direction 22 then provides air access to the air activated heater only through the openings formed by the through cut chads 14.

To increase the amount of air access to the air activated heater, the barrier film 6 is pulled in a second direction 24, opposite to the first direction. Pulling the barrier film 6 in the second direction 24, engages the partially score cut chads 16 by initially pulling on the through cut portion 18 of the score cut chads 16. By pulling on the through cut portion 18 of the score cut chad results in the partially score cut portion 20 being torn off the air access film 8, thereby resulting in air access openings being formed in addition to the air access openings that are also being formed by removal of the through cut chads 14. Varying the ratio of through cut chads 14 in relation to the partially scored chads 16 can vary the amount of air access opening area to the air activated heater. Prior to use the heater is stored in a protective film packaging.

The protective film package is of a general construction such that a structure, surface, device, product or any contents to be heated would be a base layer. An external layer of a heater package can be an inner packaging film. The inner packaging film can be attached to the base layer, or the MRE for even heating, or can be unattached to a base layer such that the heater could be used across products, containers or applications. On top of the inner packaging film is a fuel layer, this layer may be zinc, iron or any number of metals that are oxidized such that an exothermic reaction occurs when the fuel layer is in contact with oxygen in the air. The choice of metal or combination of metals in the fuel layer is dependent on the desired temperature for the heater. The fuel layer typically comprises activated carbon and the metal powder embedded in a binder. A diffusion layer is adjacent to the fuel layer. This layer may be comprised of felt or similar product. A top layer is then a porous packaging layer, a film processed as disclosed further below and referred to as an air access film, wherein a removable barrier film is secured on top of the air access film by an adhesive layer.

In further detail, the air access film is a film that is laser or mechanically processed. The air access film is processed such that the air access film comprises a pre-determined plurality of total air access openings. The size and number of air access openings is dependent on the amount of air access area needed to provide sufficient amount of air over time to achieve a desired temperature (heat) of the heater. The air access openings are created by the processing of the film to produce chads, or pieces of waste material cut from the film. The chads may be circular or oval in shape, or may have straight lines defining their perimeter such as a quadrilateral, for example diamond shaped. The particular shape is not of importance and so any shape is included herein as long as the desired amount of access and distribution of air access is achieved.

There are no limitations with respect to the size of the air access openings. Machine cutting may be used for a wide range of sizes, although the size of the air openings is less important than the distribution of openings and ratio of through cut to partially cut openings with respect to controlling air access. Laser cutting may be preferred when the access opening needed is on the order of approximately 0.030 inches or smaller. For openings approximately 0.03 inches in width or larger, mechanical processing is accurately used as well as laser processing.

Adjusting laser settings allows for an opening as small as approximately 0.005 inches in width to be made. This ultra-small opening size may be desired when total air access openings are needed, or more precise air flow is desired. Openings laser processed to be approximately 0.005 inches produce no chad. The chad essentially is ablated (evaporates) when the opening is formed.

A percentage of the total air access openings are laser or mechanically processed as a "through cut" (herein after referred to as "through cut chads") such that the laser or die has fully cut out a chad in the film which will then form an air access opening. Through cut chads are formed such that a "kiss cut" or scored hole remains on a narrow piece of the cut. A narrow piece of film remains connected from the chad to the air access film. This kiss cut or a tab allows the chad to remain in place before lamination. The width of the narrow piece that holds the through cut chad in place prior to opening is dependent on the adhesive used in lamination, film thickness and additional use factors. The kiss cut or connective piece is of a size such that the chad remains in place in the air access opening during lamination and is removed when the barrier layer is removed in either pull direction such that the entire chad is removed in either pull direction.

Such methods of forming the through cut chad include placing a "nick" in the die or mechanical cutting surface or adjusting the laser cut such that the cut is not connected end to end to form an opening. The result is a narrow tab or other uncut surface that attaches the chad to the corresponding air access opening. The narrow tab or semi-circle or other attachment mechanism allows the chad to remain in place prior to lamination but to be easily removed when the air access film and the barrier film are separated in either or both pull directions.

There may be applications where it is desired to remove the chad completely from the through cut openings while the scored opening chads remain in place before lamination and/or applying the barrier film to the air access film. In this instance, a true through cut is made and the chad is removed prior to lamination. In this application when the barrier film is pulled and removed in a first direction, no chads are removed. When the barrier film is pulled in a second direction the chads are removed providing air access to all the openings.

When the air access film without chads is desired, specifically for openings approximately 0.005 or smaller can be used for total air access as the chad will be ablated when cut.

The chad remains in place after processing and is not removed prior to lamination. The remaining plurality of total air access openings are also formed by laser or mechanical processing. However, the remaining portion of the total air access openings are formed by the laser or mechanical process making a through cut to form approximately a first half of the chad. To form the second half or remainder of the chad, the film layer is scored, that is the film is cut only partially through. This results in a chad formed with two distinct halves, a through cut half and a scored half. The chad remains in place prior to lamination as one half of the chad is only scored, or partially cut and remains secured to the air access film. The result is an air access film with a selected, pre-determined plurality of air access openings that are cut through and a selected, pre-determined plurality of air access openings defined by chads that are half through cut and half scored (hereinafter referred to as "partially score cut chads").

Further, the partially score cut chads are formed with substantially the same orientation such that the cut half of each chad is the same and oriented in the same direction. The scored half of each partially score cut chad is also oriented substantially the same such that when the air access film is viewed from a top view, the scored half of each partially score cut chads is oriented the same. The width or diameter of the openings formed once the chads are removed is determined by the amount of air access needed for the air activated heater to function, and may be of a generally accepted and standard size used in air activated heater packages.

The air access film processed as described above may be comprised of packaging films for food, films used in the construction of thermoformable splints, personal heating packs or any other products in which air activated heating is used, including metalized films or polymeric films in the approximate range of 1 mil to greater than 30 mil in thickness.

The plurality of air access openings is determined based on the structure, device, package or surface the heat will be applied to, which may include limbs and other body parts and/or the contents of a package to be heated by an air activated heater; the amount of air access needed to achieve proper desired temperature; and the amount of variation in air access desired. The total amount of air access openings will vary depending on the use of the heater, contents of the package, the weight of the package, and/or the size of the package and will be determined prior to processing of the air access film. Further, the ratio of through-cut chads to partially score cut chads is determined prior to processing based on the contents and other variables including desired temperature and air access needed to achieve said temperature. The variation in starting temperature or air temperature may also be considered when determining the ratio of through cut to partially cut air access openings. The air access layer may be used in cold and warm initial temperatures.

The depth of the score is dependent on the thickness of the air access film. In one embodiment, the air access film was processed with a score depth approximately 10-15% of the film thickness. However, the depth of the score is dependent of film composition, orientation of the film, and desired peel strength. The partially scored air access openings can be scored in the approximate range of 5% to 95% of the films thickness depending on the desired peel strength to achieve removal of the partially scored chads in one pull direction. The score must be of a depth such that the scored portion of the partially score cut chad remains attached to the film and the partially score cut chad remains in place when the barrier film is removed from the first direction. The score must also be of a sufficient depth such that when the barrier film is removed in the second opposing direction, the score is torn through and the entire partially score cut chad is removed to form the air access opening.

The air access film can comprise a monolayer or a multi-layer film construction. The score depth is greater depending on the composition of the air access film. The depth of the score is determined by mechanical testing.

Once the air access film has been laser or mechanically cut or processed, the air access film 8 is adhered to or laminated to a barrier film 6 by a light tack pressure sensitive adhesive (PSA), or other suitable adhesive for the type of film used. Hot bonding of heat lamination may also be used to adhere the air access film to the barrier film. The air access film and the barrier film would have different melting points, one of the films having a lower melting point. The films would be fed through a laminator or other heated roller system such that the film bonds together for construction of the package. "Peel Seal", or self-stick film can be used as well as any film structures used to heat laminate, bond, adhere or hot bond the barrier film and the air access film can be used in place of a PSA.

The adhesive and barrier film may be laminated to form a multi-layer product. Either the air access film or the barrier film may be adapted with extended edges 26 and 28 on opposing sides of either film. The edges may act as a tab, such that a user may hold the barrier film and use the tab for separating the films. The air access film and/or the barrier film can be adapted with an easy open feature not limited to a tab. Either film may be adapted with a flap, a pull string, a score or any other feature allowing for easy separation of the air access film and the barrier film. Separation of the films can be enhanced by adding laser or mechanical features to promote correct tear path.

To activate the air activated heater, the user may pull or otherwise separate the films. The tabs 26 and 28 or other opening features on opposing sides of the product allow the user to separate the films in either pull direction A, as represented by arrow 22 or pull direction B as represented by arrow 24. The result being that when the air access film and the barrier film are separated by removing the barrier film in pull direction B according to arrow 24, the PSA or heat laminated structure and the barrier film are removed such that the through cut chads and the partially score cut chads are fully removed, forming all of the air access openings and allowing for maximum air access through all of the openings. This may result in a higher temperature reached or the amount of heating time varied as the maximum desired amount of air access is achieved.

As discussed previously, the partially score cut chads are oriented substantially the same. The cut halves must be the first half of the chad to be pulled up when the barrier film is pulled up or off in pull direction B. This procedure removes the cut half first. With the cut half adhered to the barrier film, the scored half of the chad is detached from the air access opening film during the same pull. Thus, the scored hemispheres face or are adjacent to pull direction A, such that when the barrier film is removed from pull direction A, the scored halves remain attached to the film such that the partially score cut chads remain fully attached to the film and only the through cut chads are removed.

When less air access is desired or a lower temperature is desired, the air access film and barrier film can be separated by removing the air access layer in the opposing direction by pull direction A as represented by arrow 24. In this direction, the PSA or heat laminated structure and the layer are removed such that only the through cut-chads are removed. The through cut and partially score cut chads remain attached to the air access film such that the only holes opened for air access are the openings created by removal of the through cut chads. The result is reduced air access and a lower maximum temperature reached.

As a user may determine which pull direction is desired based on the starting temperature of the product, the desired heat needed, or the time in which the product must be heated.

The air access film and a fuel source can also be adhered to a package, structure, device or other container by a standard adhesive coating. The air access film and barrier film can be comprised of films such that the films are flexible. The heater package can also be flexible such that the heater sheets and/or heater package with the air access film and barrier film can be used in various applications and can be used to heat beverages, soups and other variously shaped platforms.

Figure 1:
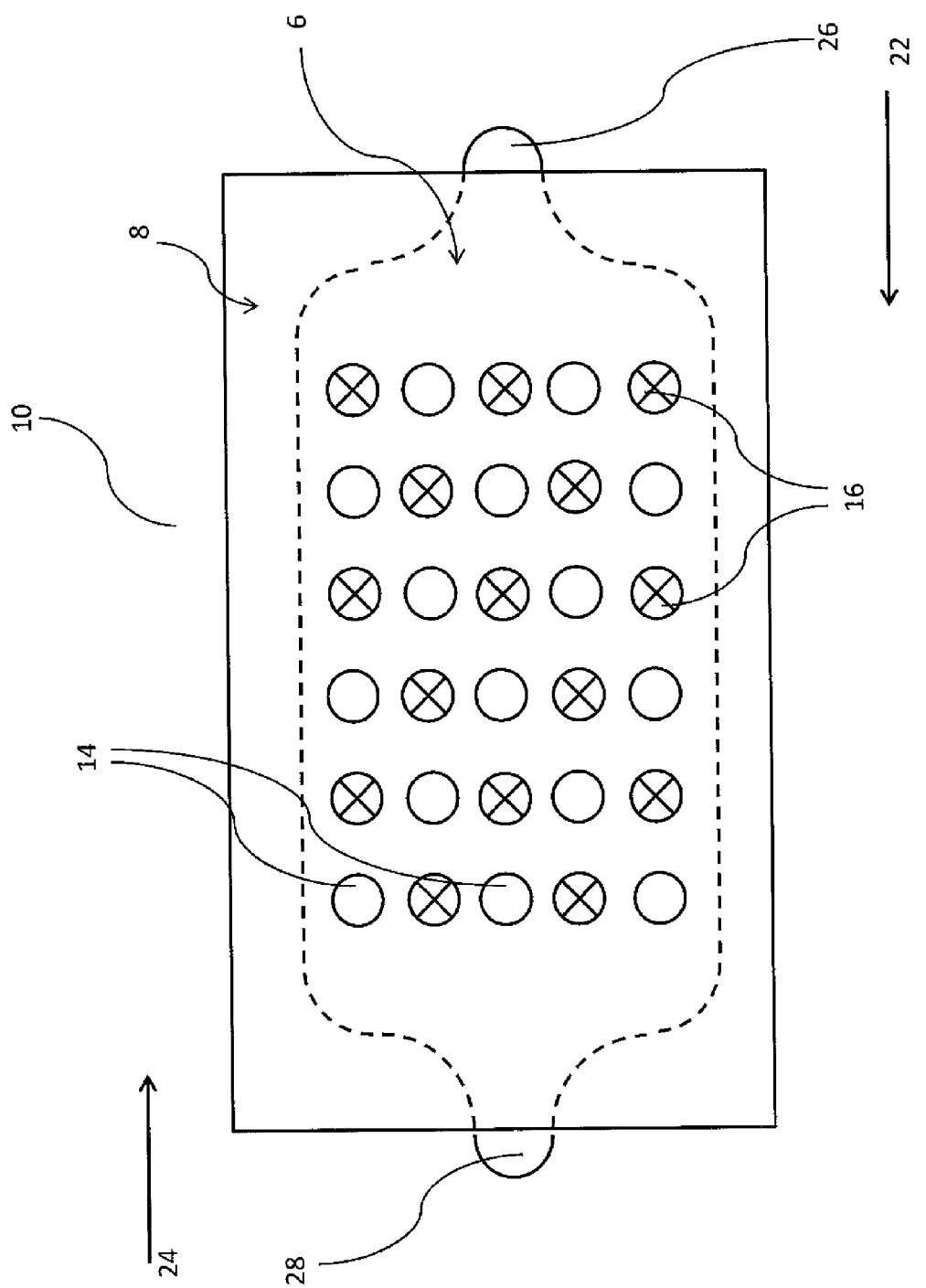
FIG. 1 is a top view of a prepared film.
Figure 3:
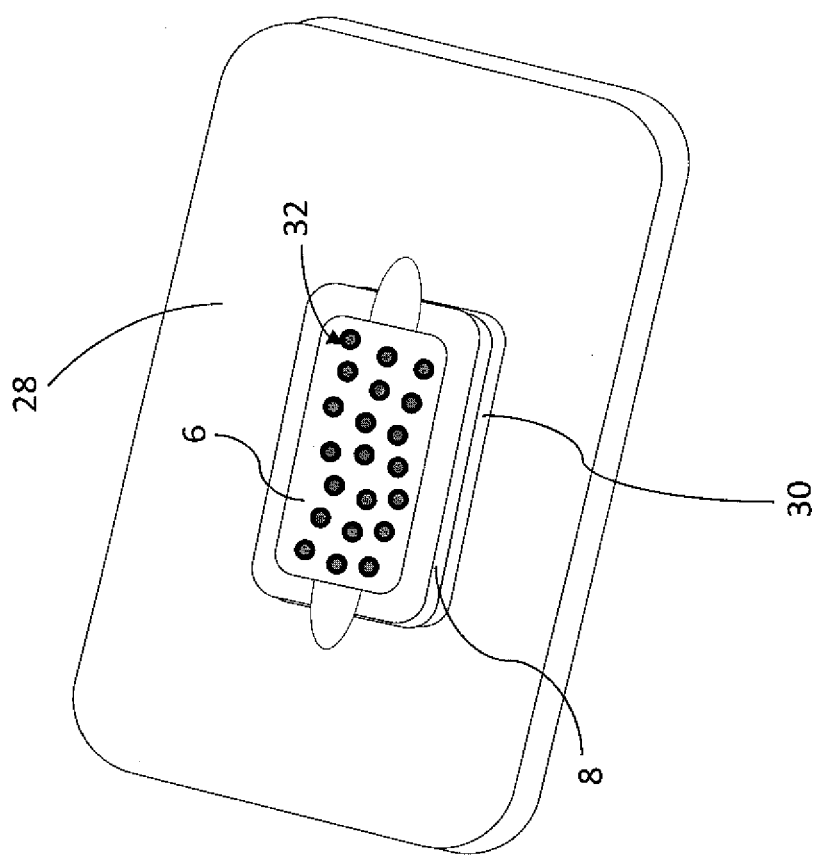
FIG. 3 is a side perspective view of an air activation layer and fuel source attached to a package.

In a further embodiment, as illustrated in FIG. 3, the air access layer and air active heating element are adhered to a package for heating a product contained therein or as attached thereto. The air access film and air activated heating system generally illustrated at 10 in FIG. 1 is adhered to a package or container 28. The first film 8, on a back side or face opposite that secured to the second film, is adhered to an outside of the package or container 28. An adhesive layer 30 may be used to secure the first layer to the package or other adhesion means similar to those described in this disclosure with respect to adhering the first and second layers to one another may also be used. The adhesion used to secure the first layer 8 to the package 28 depends on the package or container mater, construction, the fuel source used and other considerations including the strength of adhesion required. The fuel source 32 is then positioned between the package 28 and the first layer 8 having openings therein and the second layer 6 adhered thereon. Removal of the second layer allows controlled amounts of air to access the fuel source and the exothermic reaction thus heats the package 28 and any contents therein.

In another embodiment, a re-useable or re-sealable PSA may be used such that the if the user decides more heat is required, the barrier film may be replaced over the air access film and removed a subsequent time in pull direction B to remove the chads not removed when the user initially removed the barrier film in pull direction A. The reusable or re-sealable PSA may also be used with an air access film prepared with varying orientations of the through cut and scored air access openings such that multiple pulls may be used to removed different chads and further control or vary the air access to the air activated heater.

Although the present invention has been described with reference to preferred embodiments, workers skilled in the art will recognize that changes may be made in form and detail without departing from the spirit and scope of the invention.

What is claimed:

1. A variable air access mechanism, the mechanism comprising:
   a first film with a plurality of cut chads for subsequent removal to form air access openings;
   a portion of the chads formed by being only partially cut;
   a remainder of the plurality of cut chads being substantially fully cut; and
   a second film adhered to the first film wherein removal of the second film in a first direction opens all of the chads to form the air access openings or removal of the second film in an opposing direction removes only the fully cut chads.

2. The variable air access mechanism of claim 1 wherein the first film is positioned over an air activated fuel source.

3. The variable air access mechanism of claim 2 wherein the fuel source is adhered to an outer surface of a package for heating the contents of the package.

4. The variable air access mechanism of claim 1 wherein the second film comprises a reusable adhesive layer wherein the film can be removed in a first direction and replaced over the first film and removed again in an opposing direction.

5. A method of controlling air access to an air activated heater, the method comprising:
   determining a desired amount of total air access openings to be formed;
   determining a ratio of substantially fully cut chads to form a first set of air access openings to partially cut chads to form a second set of air access openings of the total air access openings to be formed;
   preparing a first film with the determined ratio of fully cut chads to partially cut chads;
   laminating a second layer on top of the first film; and
   removing the second layer in a first direction such that the total air access openings are opened or in a second direction such that only the fully cut air access openings are opened.

6. The method of controlling air access to an air activated heater of claim 5 and further comprising the step of adhering the prepared first film as an air barrier over an air activated fuel source.

7. The method of controlling air access to an air activated heater of claim 6 and further adhering the fuel source to a package for heating the contents of said package.

8. The method of controlling air access to an air activated heater of claim 5 wherein the second layer is adhered to the first film with a reusable adhesive and reapplying the second layer after a first removal and subsequently removing the barrier layer in an opposing direction.

9. An air access layer, the layer comprising:
   a base film;
   a barrier film attached to the base film; and
   wherein the base film includes a plurality of openings and a plurality of attached chads such that when the barrier film is pulled in a first direction no chads are removed and air access is provided only to the openings or when the barrier film is removed in a second direction the chads are removed and air access is provided to all openings.

10. The air access layer of claim 9 wherein the base film is further adhered as a cover over a fuel source.

11. The air access layer of claim 10 wherein the fuel source is adhered to a package and configured to heat the contents of the package upon removal of the barrier film.

\* \* \* \* \*